(12) United States Patent
Yano

(10) Patent No.: US 6,194,101 B1
(45) Date of Patent: Feb. 27, 2001

(54) PHOTOMASK, AND PROCESS AND APPARATUS FOR DETERMINING CONDITION OF PHOTOMASK

(75) Inventor: Kengo Yano, Tokyo (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 0 days.

(21) Appl. No.: 09/187,076

(22) Filed: Nov. 6, 1998

(30) Foreign Application Priority Data

Mar. 24, 1998 (JP) .................................................. 10-075429

(51) Int. Cl.[7] .............................. G03F 9/00; G01B 11/00
(52) U.S. Cl. ................................................. 430/5; 356/394
(58) Field of Search ............................... 430/5; 356/390, 356/394; 250/492.22, 310

(56) References Cited

U.S. PATENT DOCUMENTS

| | | | | |
|---|---|---|---|---|
| 4,185,298 | * | 1/1980 | Billet et al. | 358/106 |
| 5,331,407 | * | 7/1994 | Doi et al. | 356/394 |
| 5,353,116 | * | 10/1994 | Tanigawa et al. | 356/390 |

* cited by examiner

*Primary Examiner*—S. Rosasco
(74) *Attorney, Agent, or Firm*—Rabin & Champagne PC

(57) ABSTRACT

Disclosed herein are a process and apparatus for determining, with cheap and simple structure, whether a photomask is good or defective. The photomask has a mask pattern and a detection mark as parts of the pattern. The mark is formed at the same time when the pattern is formed in a mask blank. The apparatus includes a photomask holder having a hole formed through it. In a process of inspecting a photomask, it is determined whether the photomask is good by optically confirming how accurately the hole and the mark are aligned, that is, to what extent they overlap each other.

6 Claims, 2 Drawing Sheets

US 6,194,101 B1

PHOTOMASK, AND PROCESS AND APPARATUS FOR DETERMINING CONDITION OF PHOTOMASK

BACKGROUND OF THE INVENTION

1. Field of the Invention

The present invention relates to a process and apparatus for determining whether a photomask for making semiconductor devices is good or defective.

2. Background Art

A high quality photomask is necessary for the art of transferring a circuit pattern to semiconductor wafers for use in a process of making semiconductor integrated circuits. The production of a photomask includes filming a glass substrate with chrome, coating the filmed substrate with resist to make a mask blank, and describing or forming a mask pattern in the blank.

The position on a semiconductor wafer to which the mask pattern in a photomask is transferred is determined by the position of the pattern relative to the wafer. It is therefore essential for the pattern to be formed at a correct position in the mask blank.

It is therefore necessary to position a mask blank correctly relative to the position where a mask pattern should be formed in an apparatus for forming mask patterns to make photomasks. This requires the blank to be positioned correctly on a blank holder. In practical processes, however, mask blanks may not necessarily be positioned correctly. It is therefore necessary to determine whether a mask pattern is formed correctly on a mask blank. In order to confirm the position of the pattern on the blank, a coordinate measuring machine using a laser interferometer may be used. In general, however, such a coordinate measuring machine is expensive.

OBJECT AND SUMMARY OF THE INVENTION

It is therefore an object of the present invention to provide a photomask which can cheaply and securely be judged good or defective. It is another object to provide a process and apparatus for cheaply and securely determining whether a photomask is good or defective.

In accordance with the invention, a process and apparatus are provided for determining whether a photomask made of a glass substrate having a mask pattern of an opaque film is good or defective. The pattern includes a detection mark, which is formed in it when the pattern is described or formed in a mask blank. The mark has a predetermined positional relationship with the pattern. The apparatus includes a photomask holder having a hole formed through it. The hole is aligned substantially with the mark when the photomask is placed on the holder. The process includes placing the photomask on the holder, radiating light toward the hole, receiving the light which has passed through the hole and the photomask, converting the received light into an electric signal, and determining whether the photomask is good on the basis of the signal.

This makes it possible to determine whether a photomask is good by confirming the relative positions, that is to say, the degree of overlap between the photomask mark and the holder hole on the basis of the electric signal representing the quantity of light which has passed both of the hole and the mark.

BRIEF DESCRIPTION OF THE DRAWINGS

Preferred embodiments of the invention will be described with reference to the accompanying drawings, in which.

DETAILED DESCRIPTION OF PREFERRED EMBODIMENTS

Figure 1:
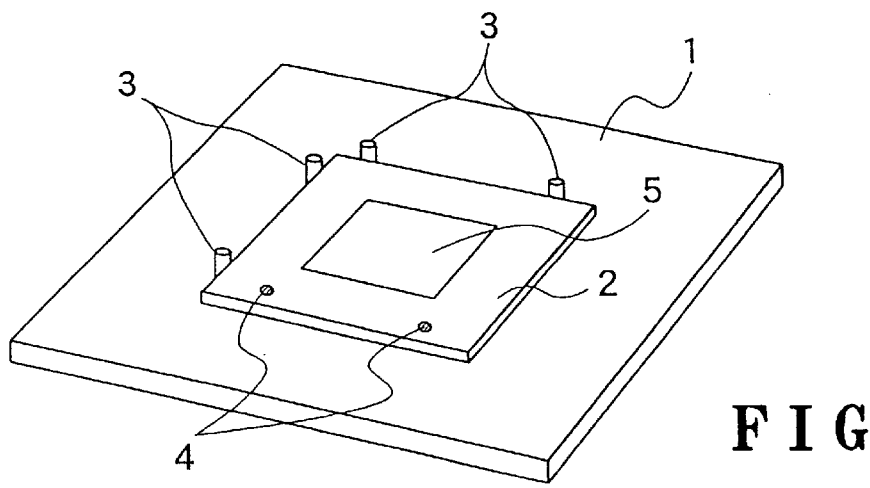
FIG. 1 is a perspective view of an essential part of an apparatus for forming a pattern, which includes a circuit pattern and detection marks, in a mask blank in accordance with the invention.

With reference to FIG. 1, an apparatus for forming a mask pattern includes a blank holder 1 and four pins 3 fixed to it. A mask blank 2 may be formed by spattering one side of a glass substrate with chrome to form an opaque film on this side, spin-coating the filmed side with resist, and prebaking the coated side to remove a surplus solvent from the resist. The blank 2 is placed on the holder 1, and positioned in place by bringing it in contact with the pins 3.

A mask pattern can be formed in the blank 2 by a pattern forming apparatus (not shown). In the pattern forming process, a circuit pattern 5 is formed together with two detection marks 4. Each mark 4 is a circle, which may be about one millimeter in diameter. The marks 4 may be formed outside the pattern area in the process of exposing the blank 2 with an electron beam. The exposed blank 2 is developed and etched to produce a photomask with the pattern 5 and the marks 4.

Figure 2:
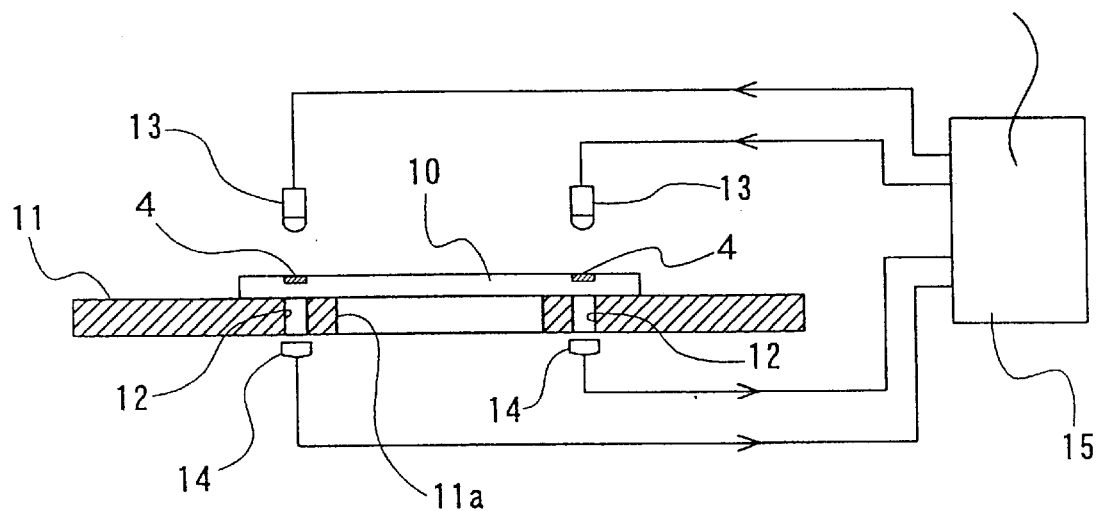
FIG. 2 is a vertical section of an essential part of an apparatus for determining whether a photomask is good in accordance with the invention in an apparatus for inspecting a photomask for defects.

With reference to FIG. 2, an apparatus for determining whether a photomask is good includes a photomask holder 11, which has a center opening 11a formed through it. A photomask 10 has a circuit pattern (not shown) and two circular detection marks 4 formed in it. The photomask 10 is positioned on the holder 11 by a suitable fixing means (not shown). The photomask 10 may then be irradiated with a scanning light beam upwardly in this figure toward the opening 11a in order for the pattern on the photomask to be inspected for defects.

The photomask holder 11 has two cylindrical holes 12 formed through it. When a good photomask 10 is positioned in place on the holder 11, the axis of each hole 12 is aligned with the axis of a respective one of the detection marks 4. It is preferable that the holes 12 be nearly equal or slightly larger in diameter than the marks 4.

Two light emitting elements 13 are positioned over the photomask holder 11. Two light receiving elements 14 are positioned under and near the holder 11. The axis of each holder hole 12 is aligned with a respective one of the emitters 13 and a respective one of the receivers 14. The light radiated from each emitter 13 passes through the photomask 10 and the associated hole 12, and is received by the associated receiver 14. The received light beams are converted into electric signals, which are sent to a control circuit 15.

The controller 15 may include a CPU, a ROM and a RAM. The controller 15 may sample the output voltages from the receivers 14 in synchronism with the drive pulses driving the emitters 13. The sampled values are added together to obtain a total signal level, which is compared with a predetermined threshold. As far as the level is equal to or higher than the threshold, it is judged that the circuit pattern is formed correctly in the photomask 10 and that the photomask is good accordingly. If the level is lower than the threshold, it is judged that the photomask 10 is defective.

The detection marks 4 may be openings formed in the chrome film of the photomask 10. In this case, if the marks 4 and holes 12 are not aligned fully because the circuit pattern is not positioned properly in the photomask 10, the chrome film outside the marks 4 prevents a sufficient quantity of light from the light emitters 13 from passing through the holes 12.

If the level of the signals output from the light receivers 14 is not sufficiently high, the controller 15 may cause a buzzer (not shown) to alarm the operator to a defect in the photomask 10.

Thus, by adding a very simple construction which consists of light emitting elements 13 and light receiving elements 14, it is possible to provide an apparatus for determining securely and cheaply in a short time whether a photomask 10 is good.

The detection marks 4, holder holes 12, light emitters 13 and light receivers 14 form two systems, which might otherwise be replaced by one system, or three or more systems. It is preferable, however, that the systems be two in number in view of possible decrease in the luminous intensity of the emitters 13, possible defects in the receivers 14, and simplification of the structure of the apparatus.

Figure 3:
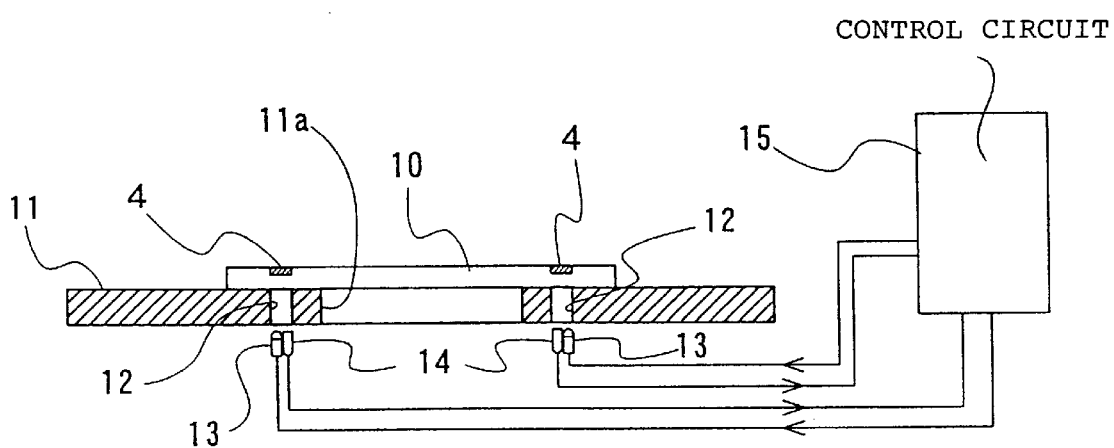
FIG. 3 is a vertical section of an essential part of another apparatus for determining whether a photomask is good in accordance with the invention in an apparatus for inspecting a photomask for defects.

With reference to FIG. 3, another apparatus for determining whether a photomask is good includes a photomask holder 11. As is the case with the apparatus of FIG. 2, the holder 11 has a center opening 11a and two cylindrical holes 12 formed through it. A photomask 10 has a circuit pattern (not shown) and two circular detection marks 4 formed in it. When a good photomask 10 is positioned in place on the holder 11, each mark 4 is aligned axially with a respective one of the holes 12.

Two pairs of light emitting elements 13 and light receiving elements 14 are positioned under the photomask holder 11. The emitter 13 and receiver 14 in each pair are close to each other and near to one of the holder holes 12. The light radiated from each emitter 13 passes through the associated hole 12, and reaches the glass substrate of the photomask 10.

If each holder hole 12 is aligned axially with the associated detection mark 4 because the circuit pattern is positioned properly in the photomask 10, the light from each emitter 13 penetrates up through the photomask substrate and the associated mark 4, where the substrate is not filmed with chrome. If each hole 12 is not aligned axially with the associated mark 4 because the pattern is not positioned properly in the photomask 10, the chrome film on the substrate reflects the light from each emitter 13. The reflected light is received by the associated receiver 14. By detecting the reflected light, it is possible to judge the IC mask pattern not positioned properly in the photomask 10.

In this embodiment, the detection marks 4 are openings (the sectional shape thereof is not limited to circular sections) formed through the chrome film. In this case, if the level of the voltages output from the light receivers 14 is lower than a predetermine threshold, the photomask 10 is judged to be good. Otherwise, the detection marks 4 might be islands of chrome film. In such a case, if the light reflected by the marks 4 is so sufficient that the level of the voltages from the receivers 14 is higher than a predetermined threshold, the photomask 10 is judged to be good.

The light emitters 13 and receivers 14 of this embodiment are positioned on one side of the photomask holder 11. This makes the optical systems more compact.

The light emitting elements 13 and light receiving elements 14 of each embodiment might be replaced by other light emitting means and light receiving means.

In each embodiment, the detection marks 4 might be formed in desired positions other than illustrated. In such a case, the holder holes 12, light emitters 13 and light receivers 14 might be positioned in association with the marks 4. The positions of the light emitters 13 and receivers 14 might be exchanged.

In each embodiment, the photomask 10 is so formed that light can penetrate through the detection marks 4. Otherwise, the marks 4 might be chrome film islands formed outside the mask pattern area. No light can penetrate through the islands.

It is to be understood that the number of the detection marks is preferably two or more in order to readily determine the condition of the photomask.

The process and apparatus for determining whether a photomask is good in accordance with each embodiment may be applied to, not only apparatus for inspecting a photomask for defects, but also apparatus for amending or correcting a photomask and apparatus for measuring the size of a mask pattern. The determining apparatus may be provided separately from the conventional apparatus.

As stated above, in each embodiment, detection marks are formed in addition to a circuit pattern in a mask blank to obtain a photomask. It is determined whether the photomask is good by optically confirming how accurately the marks are aligned with the holes formed through the photomask holder of the detecting apparatus, that is to say, to what degree they overlap each other. It is therefore possible to determine with cheap and simple structure in a short time whether a photomask is good.

What is claimed is:

1. A process for determining whether a photomask is good or defective, comprising:

providing a photomask comprising a glass substrate having a mask pattern made of an opaque film and formed on the substrate, said mask pattern including a circuit pattern and at least one detection mark that is separate from said circuit pattern;

providing a photomask holder for holding the photomask, the holder having at least one hole formed therethrough at a position aligned substantially with the detection mark when the photomask is held on the holder;

holding the photomask on the holder;

radiating light toward the hole;

receiving the light which has passed through both the hole and the photomask so as to generate an electric signal which corresponds to an amount of the received light; and determining whether the circuit pattern of said photomask is properly positioned on the photomask on the basis of a level of the electric signal.

2. A process according to claim 1, wherein the radiation of light is carried out at one side of the photomask holder and the reception of light is carried out at the other side of the photomask holder opposite to the one side.

3. A process according to claim 1, wherein the radiation of light and the reception of light are carried out at the same side of the photomask holder.

4. A process according to claim 1, wherein the determination is based on the level of the signal.

5. A process according to claim 1, wherein the mask pattern consists of a pair of detection marks, and the holder has a pair of holes passing therethrough and at positions substantially aligned with the detection marks when the photomask is held on the holder, the determination being based on the level of the sum of electric signals generated from a pair of light receiving elements which receive the light beams having respectively passed through both of the holes and the photomask.

6. A process according to claim 1, wherein the detection mark and the circuit pattern are formed at a same time, and using a same pattern forming process.

* * * * *